United States Patent [19]

Kusanagi et al.

[11] Patent Number: 4,458,242
[45] Date of Patent: Jul. 3, 1984

[54] GAS DETECTOR

[75] Inventors: Shigekazu Kusanagi, Katano; Shigeo Akiyama, Kadoma; Tohru Nobutani, Osaka, all of Japan.

[73] Assignee: Matsushita Electric Works, Ltd., Osaka, Japan

[21] Appl. No.: 302,162

[22] Filed: Sep. 14, 1981

[30] Foreign Application Priority Data

Oct. 25, 1980 [JP] Japan .............................. 55-149760
Oct. 25, 1980 [JP] Japan .............................. 55-149759

[51] Int. Cl.³ .......................................... G08B 17/10
[52] U.S. Cl. ..................................... 340/634; 422/98
[58] Field of Search ................. 340/634; 422/96, 98; 73/27

[56] References Cited

U.S. PATENT DOCUMENTS 4,045,178  8/1977  Okinaka et al. .................. 422/98
4,185,491  1/1980  Owen ............................. 340/634 X
4,256,985  3/1981  Goodson et al. ................. 340/634 X Primary Examiner—John W. Caldwell, Sr.
Assistant Examiner—Daniel Myer
Attorney, Agent, or Firm—Koda and Androlia

[57] ABSTRACT

A gas detector comprising a main gas sensing element showing the resistance change to both the detection target gases, such as methane, butane, hydrogen gases, and non-target gases such as alcohol steam, smoke; an auxiliary gas sensing element showing the resistance change primarily to non-target gases along; the first comparator to which the output based on the resistance change of main gas sensing element is received as input in parallel form; the second comparator with lower reference electric power than that of the first comparator; a gate circuit to cut off the alarm actuating signal from the second comparator by means of output induced by the resistance change of auxiliary gas sensing element. Either the output from said gate circuit or the output from said first comparator is used for alarm actuating signal of alarm circuit.

8 Claims, 48 Drawing Figures

GAS DETECTOR

BACKGROUND OF THE INVENTION

1. Field of the Invention

This invention relates to a gas detector and more particularly to a gas leak detector with improved reliability in detecting the leak of fuel gases, such as a hydrogen gas, methane gas, butane gas.

2. Prior Art

Generally, metallic oxide semiconductors, such as $SnO_2$, $ZnO$, $Fe_2O_3$, $In_2O_3$, $WO_3$, $CeO_2$, have a property to change their resistance when they come into contact with hydrogen gas, methane gas, butane gas, etc., while they are heated to high temperature. Therefore, by using said property, gas sensing element (gas sensor) to detect the leakage of fuel gases, such as LPG (liquified petroleum gas), natural gas, have been put in practical use. However, said gas identification elements are defective in selectivity to gases. That is, they have the property to show the change in resistance not only to the target gases to be detected, such as hydrogen gas, methane gas, butane gas, contained in LPG, natural gas, etc. which are consumed domestically, but also to ethanol gas, steam, which are formed during cooking. As a result, they detect also the non-target gases in addition to the target gases to be detected, thereby degrading the reliability of detection.

Consequently, a gas leak detector with highly reliable detecting performance, that is not only capable of detecting the target gases in presence solely of said target gases, such as hydrogen gas, methane gas, butane gas, but also capable of detecting said target gases in concurrent presence non-target gases which are not to be detected, such as steam, ethanol gas, smoke, without getting disrupted by the non-target gases, and furthermore, that does not transmit the detection signal to alarm circuit when the non-target gases alone are present, thereby avoiding wrong warning.

In conjunction with gas leak detection, following prior art has already been disclosed. That is, U.S. Pat. No. 3,644,795 discloses a structure, wherein highly strong gas detection elements are used by obtaining them through adding silicon compound into gas sensor components including semiconductors of metallic oxide, such as $SnO_2$, $ZnO$, $Fe_2O_3$, $NiO$ or $Cr_2O_3$, and the output induced by change in resistance of said elements is input to a buzzer. U.S. Pat. No. 3,835,529 discloses a method for preparing a gas sensing element composed of metallic oxide semiconductors, such as $SnO_2$, $ZnO$, $Fe_2O_3$, $TiO_2$, $Cr_2O_3$, $NiO$, $CoO$, through processes of mixing, forming, baking and installation of electrode. And in U.S. Pat. No. 3,732,519, a gas sensing element including a pair of electrodes and porous metallic oxides containing semiconductor particles, wherein the metallic oxides contain the particles of $Al_2O_3$ and $SiO_2$, was disclosed. However, said prior art is incapable of achieving the purpose to give the warning only when the fuel gas leakage takes place.

SUMMARY OF THE INVENTION

It is a principal object of the present invention to provide a gas leak detector with improved reliability in detecting the leak of fuel gases, such as hydrogen gas, methane gas, butane gas, etc.

In keeping with the principles of the present invention the object is accomplished by a unique gas leak detector which includes: a main gas sensing element showing the resistance change to both the detection target gases, such as methane, butane, hydrogen gases, and non-target gases such as alcohol, steam, smoke; an auxiliary gas sensing element showing the resistance change primarily to non-target gases alone; the first comparator to which the output based on the resistance change of main gas sensing element is received as input in parallel form; the second comparator with lower reference electric power than that of the first comparator; a gate circuit to cut off the alarm actuating signal from the second comparator by means of output induced by the resistance change of auxiliary gas sensing element. Either the output from said gate circuit or the output from said first comparator is used for alarm actuating signal of alarm circuit.

DETAILED DESCRIPTION OF THE INVENTION

Figure 1:
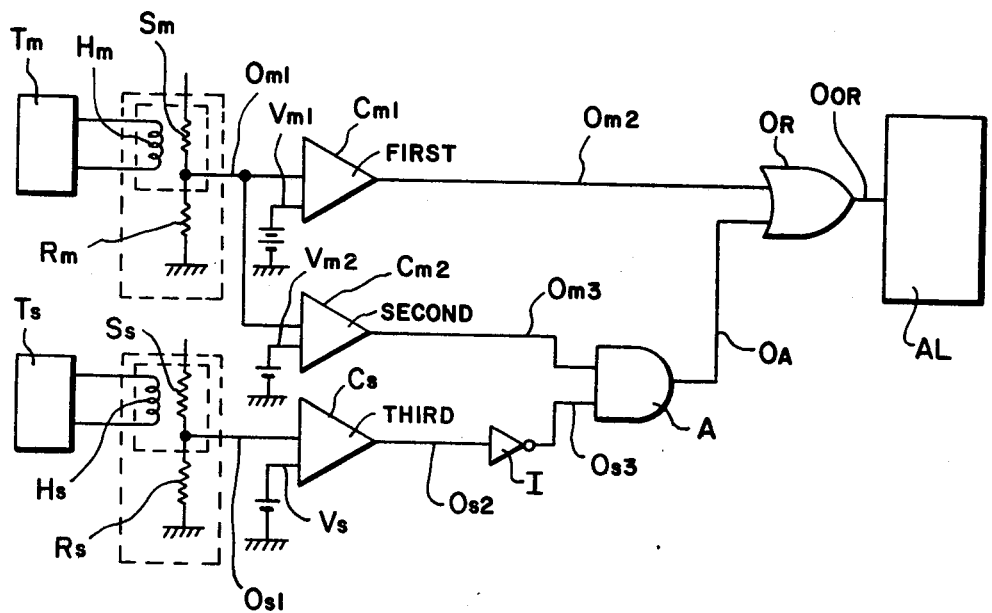
FIG. 1 is a basic circuit diagram forming a gas detector in accordance with the teachings of the present invention.

FIG. 1 is a basic circuit diagram forming a gas detector according to the present invention, showing an embodiment, wherein metallic oxides with property showing the decrease in electric resistance with increase in concentration of gases to be detected are used as gas sensing element.

As shown in the figure, said embodiment includes a main gas sensing element (sensor) Sm showing the marked change in resistance by the contact of not only the target gases, but also the non-target gases; and an auxiliary gas sensing element Ss showing the greater change by the contact of non-target gases than by the contact of target gases. The main gas sensing element Sm and the auxiliary gas sensing element Ss are heated and maintained at the temperature where the marked resistance change occurs due to contact of respective gases. For said purpose, sensor elements Sm and Ss include heaters Hm and Hs, respectively, and said heaters Hm and Hs are controlled to be kept at the element heating temperature where the resistance change rate shows its ultimate point, by temperature control circuits Tm and Ts provided with voltage circuits.

Prior to giving the description on the gas detection circuit, the description on the element will hereunder be given. As main gas sensing elements shown in FIG. 1, metallic oxides, such as $SnO_2$, $ZnO$, $Fe_2O_3$, $WO_3$, $CeO_2$, $In_2O_3$, are used. Said metallic oxides are known to have the properties that they differ in resistance depending on the type of gases when the concentration of the gases is constant, and that, even when the gases are identical in type, said metallic oxides differ in resistance depending not only on the temperature at which they are maintained, but also on the concentration. Therefore, a specified resistance change caused when the concentration of leaking gas reaches to a specified point can be effected to produce a specified output through applying a specified voltage, and the detection signal can be obtained through comparing said output with reference voltage set up to be at specified level.

The description on the gas detection circuit will hereunder be given.

Said main gas sensing element Sm and its pairing counterpart, auxiliary gas sensing element Ss, are connected in series to resistors Rm and Rs, respectively. When the DC voltage is applied to the both ends of the foregoing series circuits, the resistance changes of the main gas sensing element Sm and auxiliary gas sensing element Ss are detected as both end voltages of each of resistors Rm and Rs, and the outputs Om 1 and Os 1 induced by those respective resistance changes are obtained. In other words, the main gas sensing element Sm and the auxiliary gas sensing element Ss make up the output circuit of gas sensing elements that obtains the outpus Om 1 and Os 1 induced by the resistance change caused by the contact with gas.

In said gas detection circuit, there is included a first comparator to which the output Om 1 induced by the resistance change in main gas sensing element Sm is received as input and a second comparator Cm 2 disposed in parallel with said first comparator. The reference voltage Vm 2 of said second comparator Cm 2 is set to be lower than the reference voltage Vm 1 of the first comparator Cm 1.

On the other hand, also the third comparator Cs to which the output Os 1 induced by the resistance change in auxiliary gas sensing element Ss is received as input, is included in said gas detection circuit. The reference voltage of said comparator Cs is set at Vs.

In addition, by considering that the output Os 2 from the third comparator comes from and is controlled by the auxiliary gas sensing element's specific property showing the increase of its electric resistance in parallel with increase in concentration of the gas to be detected, an inverter I for inverting said output Os 2 is provided. There is also an AND circuit A receiving the output Os 3 of said inverter I as well as the output Om 2 of the second comparator Cm 2 as inputs. Said AND circuit A forms a gate circuit for blocking the alarm actuating signal from the second comparator Cm 2 by means of the output Os 3 induced by the resistance change of auxiliary gas sensing element.

Then there is an OR circuit Or for using either the output OA from the AND circuit A obtained based on the property of AND circuit A forming the gate circuit, or the output Om 2 from the first comparator Cm 1, as alarm actuating signal of an alarm circuit AL. By said alarm circuit AL, a warning indication as to the gas detection is given. For expressing said warning, the widely known means, such as giving out an audible sound, emitting a visible light, are used without limit in type of the means.

Next, the description will be given on operation depending on the presence or absence of target and non-target gases which induce the resistance change in respective gas sensing elements Sm and Ss.

(1) In absence of both target and non-target gases no resistance change occurs in main sensing element Sm as well as in auxiliary gas sensing element Ss, including metallic oxides having the property to decrease the electric resistance with increase in concentration of gas to be detected. Accordingly, the respective outputs Om 2, Om 3, and Os 2 from the first comparator Cm 1, the second comparator Cm 2, and the third comparator Cs become a low (L) level. Then, although the L level output Os 2 obtained from the third comparator Cs is inverted in the inverter I to a high (H) level, in the AND circuit A that applies the logical product with L level output Om 3 obtained from the second comparator Cm 2, the output OA is obtained as L level output, and in the OR circuit Or where the logical sum of said output OA and L level output Om 2 from the first comparator Cm 1 is used, the Oor is obtained in L level. By said L level output Oor, the alarm circuit is not actuated. It means that the warning is not given when both the target and non-target gases are absent.

(2) In presence of detection target gases alone. In the auxiliary gas sensing element Ss, a slight decrease in resistance occurs in proportion to the concentration of the target gas, by the contact with said target gas, and induced by said decrease in resistance, the output Os 1 is obtained. The output Os 3 from the third comparator Cs with reference voltage set at higher level than that of said output Os 1 can be obtained with L level. Said L level output Os 2 is increased in the inverter I, and the output Os 2 is obtained in H level.

On the other hand, in the main gas sensing element Sm, a decrease in resistance proportional to the target gas concentration is caused, and in response to said resistance decrease, the output Om 1 comes out. When said output Om 1 is higher in level than that of the reference voltage set up in the second comparator Cm 2, the output Om 3 is obtained in H level from the second comparator Cm 2.

Consequently, the inputs of the AND circuit A derived from the outputs Om 1, Os 1, from both the main gas sensing element Sm and the auxiliary gas sensing element Ss are of H level, therefore, from said AND circuit A, the H level output OA is obtained. Said H level output OA is processed in the OR circuit Or to obtain the logical sum with the L level output from the first comparator Cm 1, and the H level output Oor is result from said process in OR circuit Or, then, by said output Oor, the alarm circuit AL is actuated. It means that, in presence of the detection target gas alone, the target gas is detected.

When the output Om 1 induced by the contact with target gas with high concentration is higher in voltage level than the reference voltage of the first comparator Cm 1 where the reference voltage is set to be higher than that of the second comparator, from said first comparator Cm 1 the H level output Om 2 is obtained as alarm actuating signal, without needing the use of the output from the second comparator for alarm driving signal.

(3) In presence of only the non-target gas. In the main gas sensing element, by the contact of non-target gas, the decrease in resistance proportional to the concentration of said non-target gas, and induced by said decrease, the output Om 1 is obtained. When said output Om 1 is higher in level than that of the reference voltage Vm 2 of the second comparator Cm 2, the output Cm 3 is obtained in H level.

Meantime, also the resistance of auxiliary gas sensing element Ss lowers, and according to said decrease, the output Os 1 is obtained. When said output Os 1 is higher in level than the reference voltage Vs of the third comparator Cs, the H level output Os 2 is obtained from the third comparator Cs. Said output Os 2 is inversed in the inverter I, and the L level output Os 3 is obtained. In the AND circuit A that takes the logical product of said L level output Os 3 with the output Om 3 from the second comparator Cm 2, the L level output Oa is obtained. In this case, because the output Om 2 from the first comparator Cm 1 is in L level, the L level output Oor is obtained in the OR circuit Or. In other words, the non-target gas is not detected, and the alarm circuit AL is not actuated.

However, even though the gas in presence is the non-target gas, when the output Om 1 with higher in level than the reference voltage Vm 1 is of the first comparator Cm 1 is obtained by the main gas sensing element Sm due to the presence of non-target gas with high concentration, Om 2 becomes H level, causing the actuation of the alarm driving signal.

(4) In concurrent presence of non-target and target gases. The main gas sensing element Sm and the auxiliary gas sensing element Ss show the corresponding decrease in resistance by getting affected by summed up concentrations of non-target gas and target gas, and according to the respective decreases, the outputs Om 1 and Os 1 are obtained.

First, when the output Os 1 is higher in level than the reference voltage of the third comparator Cs receiving the output Os 1 from the auxiliary gas sensing element Ss as input, the H level output Os 2 is obtained from the third comparator Cs and said output Os 2 is inverted to L level in the inverter I.

On the other hand, when the output Om 1 from the main gas sensing element Sm is induced by the target gas presenting in so extremely micro amount that it is unworthy for detection, if said output Om 1 is lower in level than the reference voltage of the second comparator Cm 2, the output Om 3 from the second comparator Cm 2 is obtained as L level.

As the result, from the AND circuit A receiving the L level output Os 3 and the L level Om 3 as inputs, the H level output is not obtained and the alarm actuating signal is not given. That is, if the alarm driving signal is given at this point, it falls in the range of erroneous signal.

On the other hand, the output Om 1 of the main gas sensing element receiving the summed up effect of concentrations of target gas and non-target gas includes the output due to the non-target gas. Although, when the output Om 1 in this case reaches to the higher level than that of the reference voltage of the second comparator Cm 2, the output Om 3 of the second comparator Om 2 is obtained in a form of H level alarm actuating signal, it is blocked by the output from the auxiliary gas sensing element Os 3 inputted to the AND circuit which forms the gate circuit. However, since the output Om 3 from the second comparator Cm 2 contains the output derived from the non-target gas as noise, the concentration of the target gas in so extremely micro amount and thus unworthy to be detected does not apply to the detection failure.

When the output Om 1 from the main gas sensing element affected by summing-up effect corresponds to the gas concentration causing the output higher in level than the reference voltage Vm 1 of the first comparator Cm 1, the output Om 1 from the first comparator Cm 1, the output Om 1 from the first comparator Cm 1 is obtained in H level, and the alarm actuating signal is given regardless of the output Oa from the AND circuit A.

The following table shows the operations described above in relation to the presence or absence of the target and the non-target gases by which the resistance change in respective gas sensing element Sm, Ss, is induced as mentioned above, together with operations in some other example cases.

TABLE 1

|  | IN PRESENCE OF NON-TARGET GAS FOR DETECTION | | IN PRESENCE OF DETECTION TARGET GAS ALONE | | NEITHER DETECTION TARGET GAS NOR NON-TARGET GAS ARE PRESENT |
| --- | --- | --- | --- | --- | --- |
|  | TARGET GAS ABSENT | EXTREMELY MICRO AMOUNT OF TARGET GAS PRESENT | HIGHLY CONCEN-TRATED TARGET GAS PRESENT | DETECTION TARGET GAS/LOW CONCENTRATION PRESENT | DETECTION TARGET GAS HIGH CONCENTRATION PRESENT |  |
| Om 2 | L | L | H | L | H | L |
| Om 3 | H | H | H | H | H | L |
| Os 2 | H | H | H | L | L | L |
| Os 3 | L | L | L | H | H | H |
| Oa | L | L | L | H | H | L |
| Oor | L | L | H | H | H | L |
| WARNING | NOT GIVEN | NOT GIVEN | GIVEN | GIVEN | GIVEN | NOT GIVEN |

Also, since the proposed gas detector operates as mentioned above, it does not give the wrong warning by the presence of non-target gas formed during cooling, etc. Furthermore, it reliably gives the warning even when the leak of the target gas is in only micro amounts.

Figure 2:
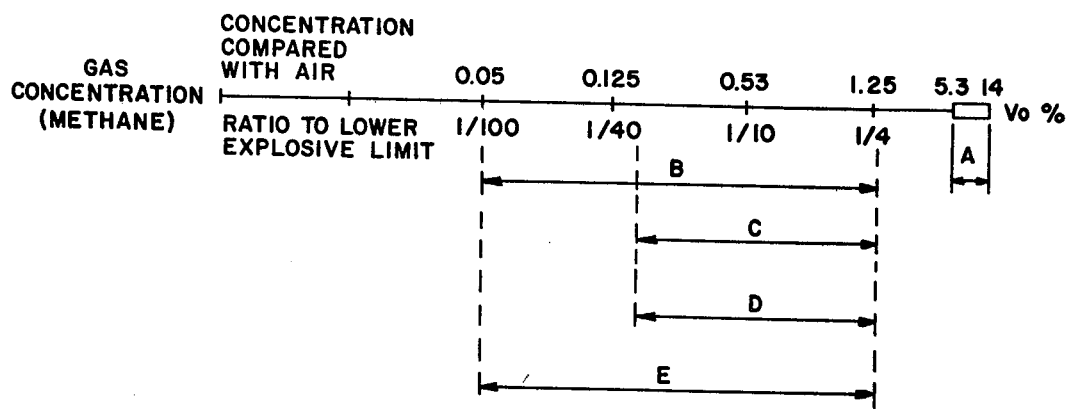
FIG. 2 shows a concrete description of the effect accomplished by the present invention.
Figure 3:
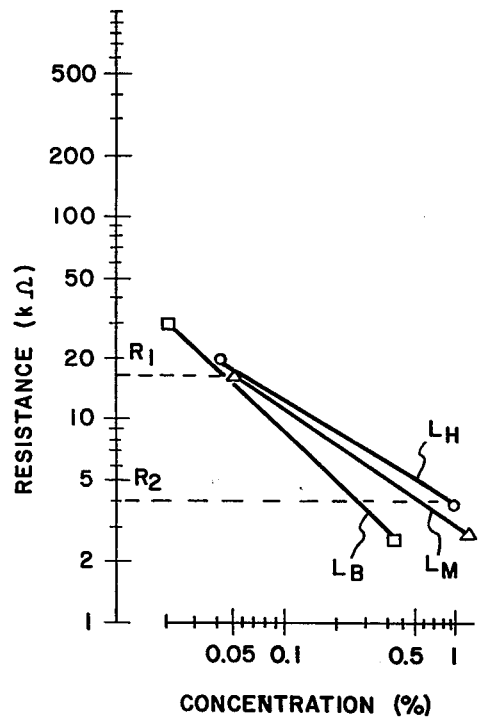
FIGS. 3 to 24, 26 to 43 and 45 to 48 show graphical representation showing the relationship between the concentration of gas and the resistance value.
Figure 4:
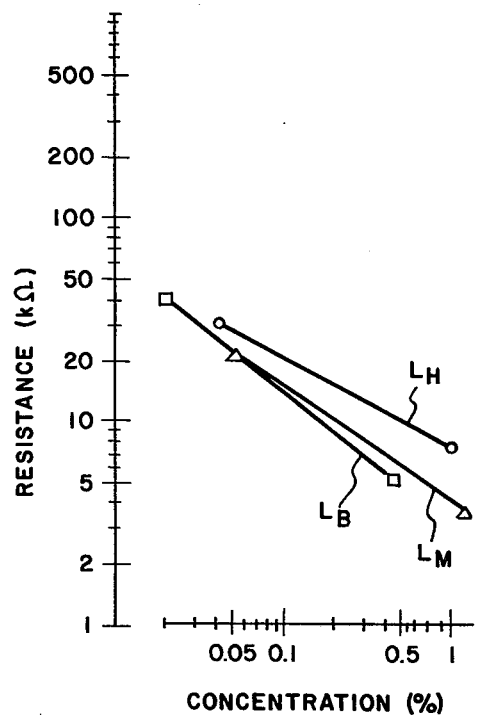
Figure 5:
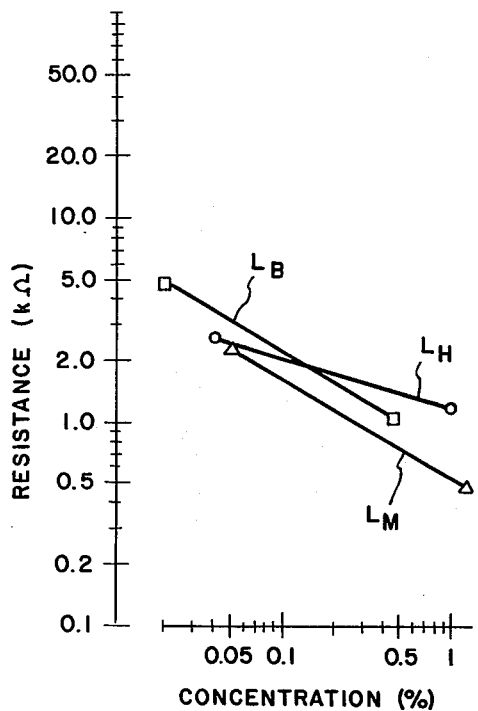
Figure 6:
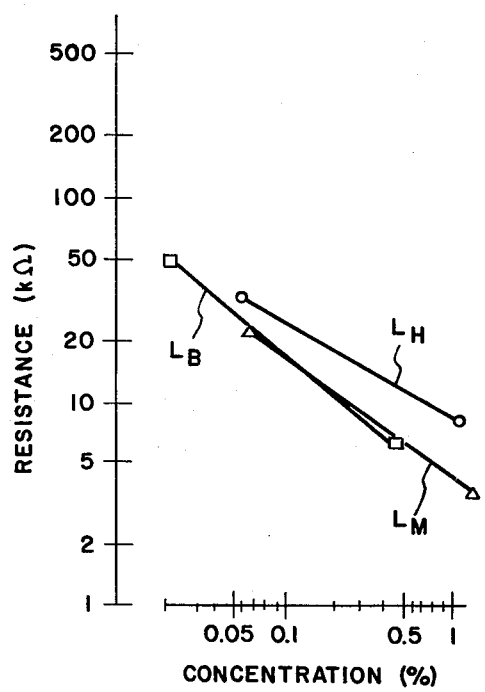
Figure 7:
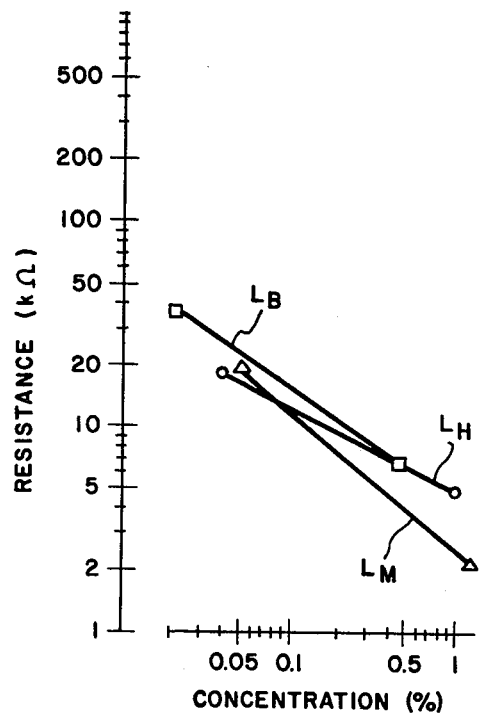
Figure 8:
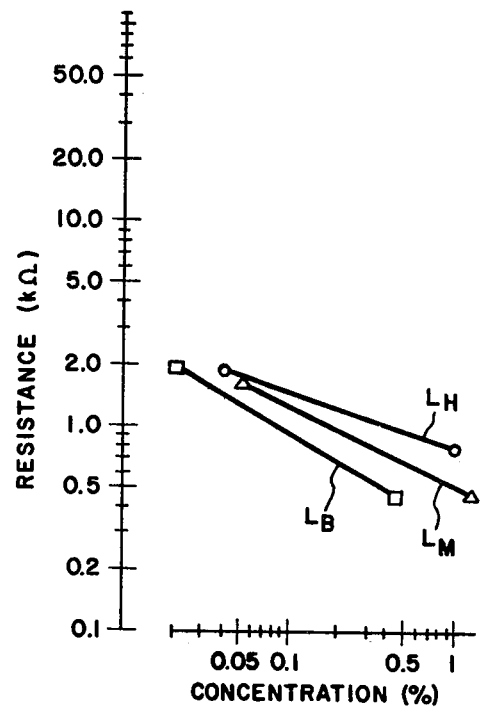
Figure 9:
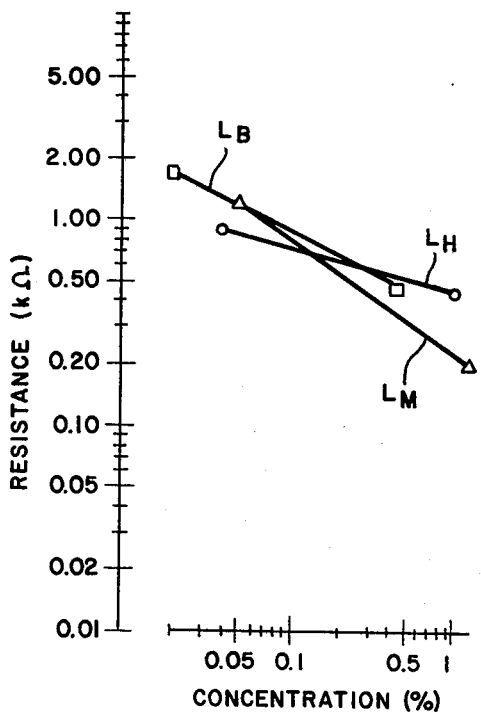
Figure 10:
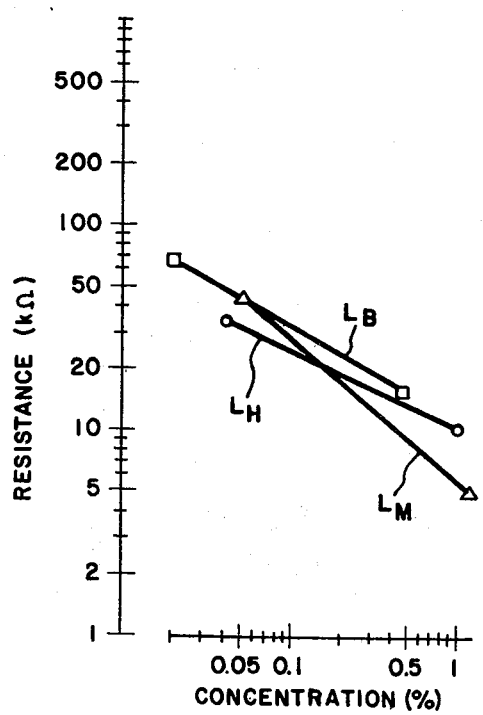
Figure 11:
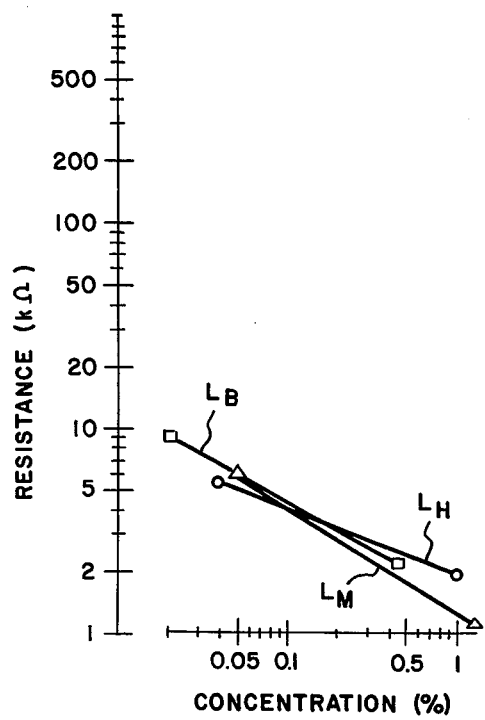
Figure 12:
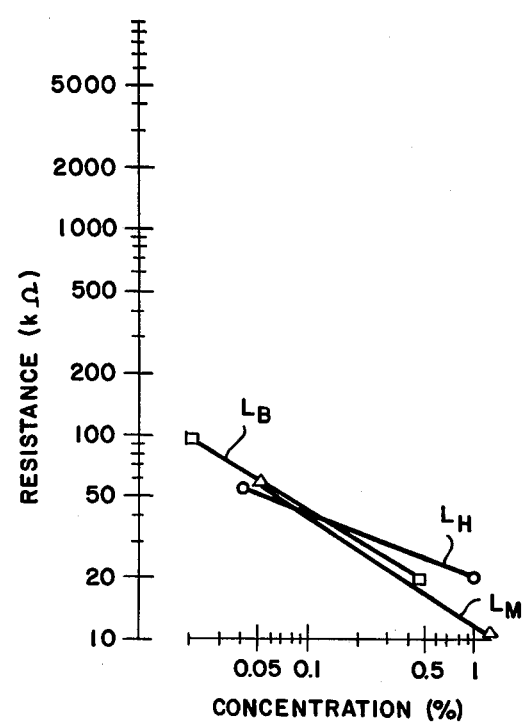
Figure 13:
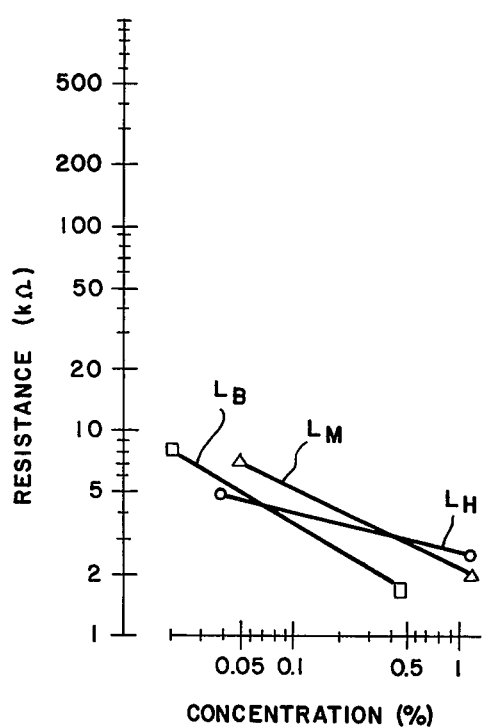
Figure 14:
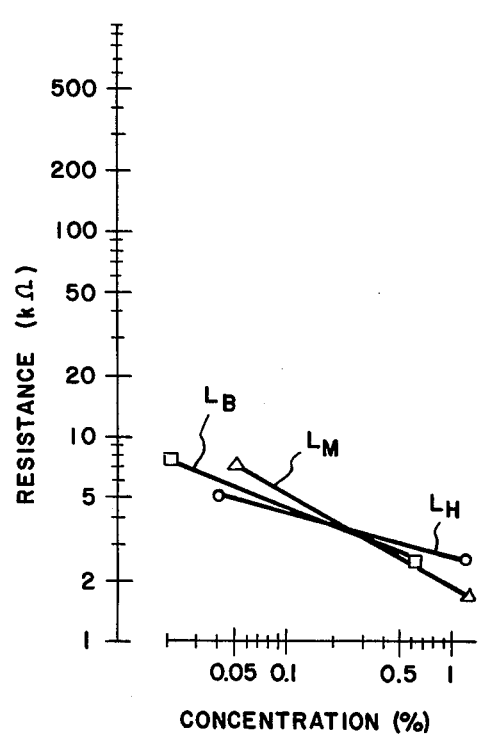
Figure 15:
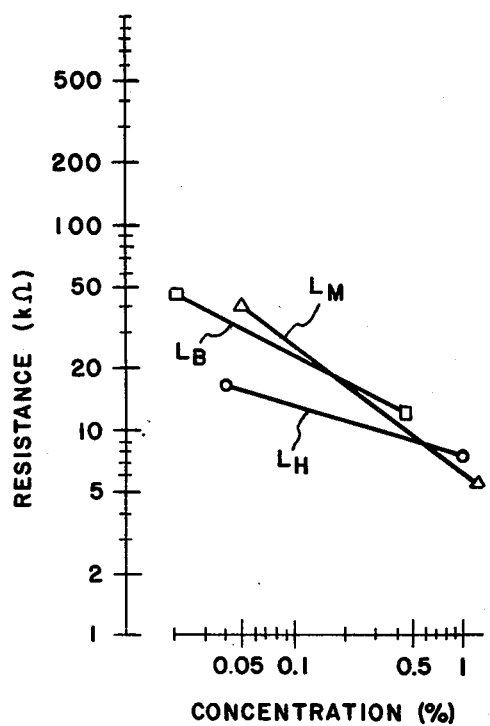
Figure 16:
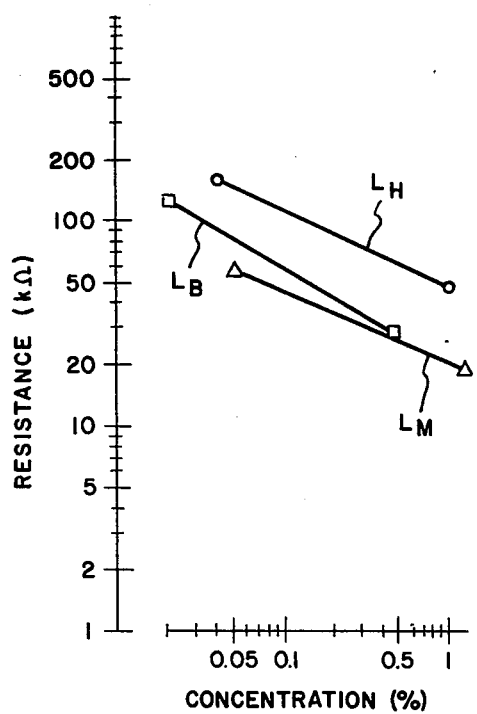
Figure 17:
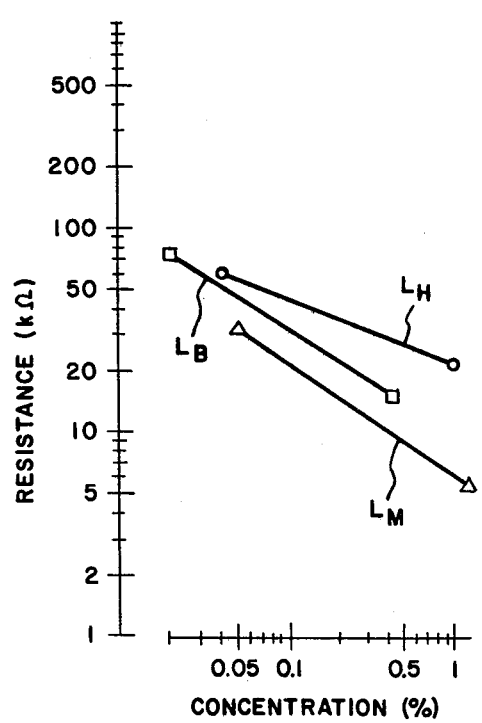
Figure 18:
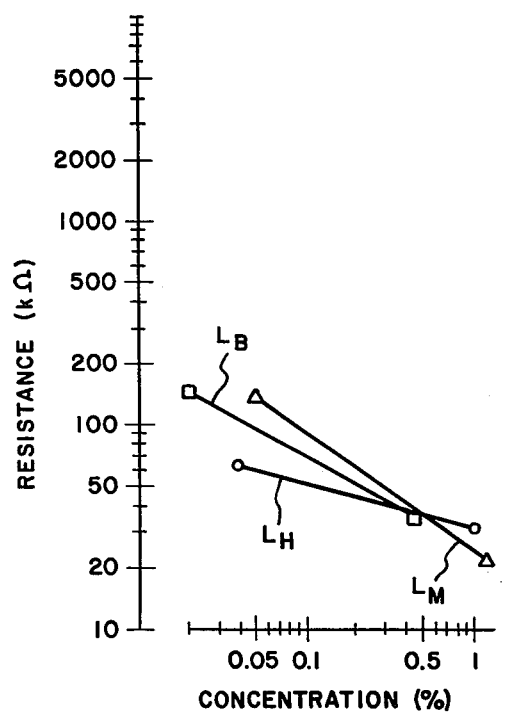

The further concrete description will hereunder be given on the effect shown by said gas detector with reference to FIG. 2, by selecting, as examples, methane that is a primary component of natural gas as target gas, and alcohol, as non-target gas. The lower limit of concentration for starting the alarm, prescribed by the inspection standard must be within the range shown by symbol B in FIG. 2. However, in the conventional gas detectors, the detection sensitivity is lowered in order to avoid the noise due to non-target gas, therefore, their capability is limited to detect only the gas leak within the range shown by symbol C. On the other hand, in the proposed gas detector mentioned above, because the noise due to the non-target gas can be eliminated, the detecting capability is enhanced, and the target gas can be detected in the range shown by symbol E in FIG. 2, i.e., in the range equal to that prescribed by the inspection standard.

Said gas detector proposed requires the main gas sensing element for detecting the presence of fuel gas, as mentioned previously. However, as the conventional inflammable gas sensing element has the following problems, the improvement has been needed. That is, there was a problem that, when the conventional gas sensing element is used for a town gas leak alarm, the concentration level for actuating alarming differs largely depending on the type of town gases. For example, there was a tendency that the warning is not given for the town gas composed primarily of liquified natural gas (LNG) until the concentration reaches too high a level, while the warning is given even at a low in concentration level if the town gas is composed mainly of liquified petroleum gas (LPG). The reason for the above is that the conventional gas sensing elements are lower in sensitivity to methane ($CH_4$) gas, that is a main component of LNG, than to butane ($C_4H_{10}$) gas, that is a primary component of LPG. However, the aforesaid problem cannot be solved simply by increasing the sensitivity to methane gas. In other words, because the lower explosive limit (LEL) of methane is 5.6 vol. % while the lower explosive limit of isobutane is 1.8 vol. %, the relative sensitivity to butane must be higher than to methane. Furthermore, as the lower explosive limit of hydrogen ($H_2$) gas that is used generally as town gas is 4 vol. %, an appropriate relative sensitivity must be shown also to it.

As should be apparent from the foregoing description, for the gas sensing elements to be suitable as applied to gas leak alarm for town gas, as far as there are various town gases composed mainly of methane, butane or hydrogen, it is necessary to have the well balanced sensitivity to said 3 types of main component gases.

With aforementioned circumstances in mind, the present invention is intended to provide a gas sensing element capable of meeting the foregoing requirements.

That is, a gas sensing element according to the present invention is characterized by that, it includes the components capable of detecting the gases, i.e., its effective components include indium oxide one type selected from a group composed of α form ferric oxides, and palladium oxide.

The further detailed description hereunder will be given on said gas sensing element.

One form of the embodiments of gas sensing element according to this invention is that wherein as the effective components, 3 types, i.e., indium oxide, tin oxide, and palladium oxide, are used, and in order to improve as well as to balance the sensitivity to various gases, the 3 types of components with respective features are mixed for use. Furthermore, if $PtO_2$ or $RH_2O_3$ is added as the fourth component to said $In_2O_3$—$SnO_2$—$PdO$ system, the sensitivity to hydrogen gas can be improved by $PtO_2$ added, and the concentration dependence to each of gases can be improved by $Rh_2O_3$ added, respectively.

Each oxide included in the element may take various oxidation forms as it has plural types of valancies, and there is no restriction imposed on said oxidation forms. Also, as to the oxides having the plural types of oxidation forms, there may be the cases wherein that with any of the oxidation forms is in element as single component, or there may be cases, wherein those with plural types of oxidation forms are concurrently presenting in element. In the oxidation forms referred to here, those with non-stoichiometric composition due to lattice defect, etc. are included.

However, usually, indium oxide takes the oxidized form of $In_2O_3$, tin oxide is in oxidized form $SnO_2$, and palladium oxide takes the oxidized form of PdO. Accordingly, in dealing with the ratio of components (composition ratio) forming the element in this specification, every oxide is assumed to be taking the oxidation form among those shown above. Also, there are the cases that In, Sn, Pd are included in gas sensing element in the form of element, but also in such cases, the composition ratio is calculated by assuming those elements to be in the form of above-mentioned oxides.

The characteristic points of the gas sensing element according to this invention are that it contains the aforesaid 3 types of components with the following relative ratio: in total of effective components, indium oxide takes up the ratio of 25~50% by weight (hereinafter, abbreviated as %), tin oxide occupies 75~50% of total weight and palladium oxide occupies 0.06~5% of the total weight and also that, preferably, the composition ratio is set to be 35~45% for indium oxide, 65~55% for tin oxide, and 0.06~5% for palladium oxide. When indium oxide exceeds 50%, the resistance value of the element becomes too small, causing the problem in formation of alarm circuit. Also, there rises the problem that the sensitivity to hydrogen and butane is lowered in comparison with that to methane. When tin oxide exceeds 75%, the concentration dependence to hydrogen decreases, and the sensitivity at high concentration lowers. When palladium oxide exceeds 5%, the resistance value of element decreases, and the sensitivity to respective gases lowers. When the quantity of palladium oxide decreases to below 0.06%, the sensitivity to methane is lost.

Upon preparation of gas sensing element, sometimes components functioning as binder, or those serving as extender, etc. are added into the components showing the gas sensing capability. Even in such cases, as far as the components showing the gas sensing capability include indium oxide, tin oxide, and palladium oxide, they are included in the scope of the present invention. The very reason for describing in this specification that the effective components include the foregoing 3 types of oxides comes from the consideration on the frequent practices of adding the components other than those showing the gas sensing capability upon actual preparation of the gas sensing element. However, in spite of the foregoing description, needless to say, the cases wherein the combustible gas sensing element includes only the effective components as mentioned above are included in the scope of the present invention, and the foregoing description implies no intention to exclude such cases from the scope of the present invention.

As a form of combustible gas sensing element according to this invention, generally, the sintered form is preferred on the grounds that a satisfactory gas sensitivity can be obtained readily, and that it is highly stable against time lapse, etc. However, the form is not limited to the above, and any forms, such as thin film, thick film, can be used freely. Also, the preparation material, preparation method, etc. can be flexibly selected depending on the availability of material, cost, application, purpose, etc. There is no restriction on the type of the starting material for preparation (material can be the target oxides themselves) as far as they give indium oxide, tin oxide, and palladium, at the point when they are made into element. Also, any intermediate treatment can be given to starting material, if necessary.

As mentioned previously, hydrogen, butane, and methane have the different lower explosive limit values of 4%, 1.8%, and 5.6%, respectively. According to the present invention, the gas sensing elements showing the equal sensitivity to gases regardless of the types of the gases, at the gas concentration levels of 1/100, 1/10, ¼, etc., measured by using the aforesaid lower limit values as standards, respectively, can be obtained. Consequently, by the use of the gas sensing element according to this invention, no matter what type of gas is in presence, the dangerous state due to its presence can be detected with almost equal sensitivity to all of such gases. Therefore, the town gases including various gas components can be monitored for their leak by using the same gas leak alarms, thus, said gas sensing element can be regarded as ideal for the application to domestic gas leak alarm.

Next, the description will be given on the embodiments of this invention as well as on the comparison embodiments.

As material powders, In$_2$O$_3$ (Yamanaka Semiconductor Co., Ltd., 99.99%), SnO$_2$ (Yamanaka Semiconductor Co., Ltd., 99.99%), and PdO (Nakarai Kagaku Yakuhin Co., Ltd., GR-grade) were selected, and they were compounded with the ratio so that the composition of each element becomes equal to that in Table 2 (shown later). Then, after thoroughly mixing the material powders by using a grinder (total amount 1 g-30 minutes), the mixed powder was weighed to portion out a specified amount (15 mg), and formed into cylindrical element of 2 mm $\phi$ in diameter and 2 mm in length, with 2 platinum electrodes (diameter 0.2 mm $\phi$, length 15 mm) embedded in parallel in it, by compression forming (pressure 1~2 t/cm$^2$). Then, by baking under the conditions of 600° C., 700° C., 750° C., or 800° C., in baking temperatures, 1~3 hr in baking time, in air, the element, i.e., the gas sensor (sinter) was prepared.

The X-ray analysis showed that respective oxides composing the gas sensor are presented in mixed state. Also, it was revealed through analysis by using the X-ray microanalyzer that the dispersion of respective components was quite homogeneous. It was also confirmed by ESCA (Photoelectronic spectroscopic analysis) that sometimes palladium oxide is partially reduced to metallic palladium, but in the present invention, said metallic palladium was also regarded as palladium oxide and included in palladium oxide in the calculation of composition ratio.

Around each gas sensor obtained as mentioned above, a coiled form heater was provided, and also, for explosion-proof, a stainless steel wire net cap was provided as cover, to obtain a gas sensing unit.

TABLE 2

| | COMPOSITION OF ELEMENT (% BY WEIGHT) | | | | | BAKING TEMP. (°C.) | PERFORMANCE | | DRAWING NUMBER |
|---|---|---|---|---|---|---|---|---|---|
| | | | | FOURTH COMPONENT | | | E (—) | INTERMEDIATE RESISTANCE VALUE (KΩ) | |
| | In$_2$O$_3$ | SnO$_2$ | PdO | PtO$_2$ | Rh$_2$O$_3$ | | | | |
| EMBODIMENT 1 | 29.4 | 68.6 | 2.0 | | | 600 | 4.12 | 8.07 | 3 |
| EMBODIMENT 2 | 29.4 | 68.6 | 2.0 | | | 700 | 2.95 | 12.70 | 4 |
| EMBODIMENT 3 | 29.4 | 68.6 | 2.0 | | | 800 | 1.93 | 1.64 | 5 |
| EMBODIMENT 4 | 29.7 | 69.3 | 1.0 | | | 800 | 4.00 | 16.00 | 6 |
| EMBODIMENT 5 | 39.2 | 58.8 | 2.0 | | | 600 | 2.74 | 11.13 | 7 |
| EMBODIMENT 6 | 39.2 | 58.8 | 2.0 | | | 800 | 2.17 | 1.14 | 8 |
| EMBODIMENT 7 | 38.0 | 57.0 | 5.0 | | | 600 | 1.99 | 0.65 | 9 |
| EMBODIMENT 8 | 38.0 | 57.0 | 5.0 | | | 800 | 2.25 | 23.06 | 10 |
| EMBODIMENT 9 | 47.5 | 47.5 | 5.0 | | | 600 | 2.59 | 3.42 | 11 |
| EMBODIMENT 10 | 26.1 | 71.8 | 2.1 | | | 750 | 2.75 | 32.88 | 12 |
| EMBODIMENT 11 | 29.4 | 68.6 | 1.5 | 0.5 | | 600 | 1.96 | 3.40 | 13 |
| EMBODIMENT 12 | 39.4 | 58.8 | 1.5 | | 0.5 | 600 | 1.86 | 3.66 | 14 |
| COMPARISON EMBODIMENT 1 | 19.6 | 78.4 | 2.0 | | | 600 | 1.39 | 13.78 | 15 |
| COMPARISON EMBODIMENT 2 | 19.6 | 78.4 | 2.0 | | | 700 | 1.19 | 52.94 | 16 |
| COMPARISON EMBODIMENT 3 | 19.6 | 78.4 | 2.0 | | | 800 | 1.47 | 26.13 | 17 |
| COMPARISON EMBODIMENT 4 | 9.8 | 88.2 | 2.0 | | | 800 | 1.77 | 46.88 | 18 |
| COMPARISON EMBODIMENT 5 | 49.0 | 49.0 | 2.0 | | | 800 | 1.87 | 0.23 | 19 |
| COMPARISON EMBODIMENT 6 | 66.5 | 28.5 | 5.0 | | | 600 | 1.40 | 0.42 | 20 |
| COMPARISON EMBODIMENT 7 | 30.0 | 70.0 | 0 | | | 600 | 0.54 | 6.99 | 21 |
| COMPARISON EMBODIMENT 8 | 30.0 | 70.0 | 0 | | | 800 | 1.31 | 1.83 | 22 |
| COMPARISON EMBODIMENT 9 | 36.0 | 54.0 | 10.0 | | | 600 | 1.62 | 15.77 | 23 |
| COMPARISON EMBODIMENT 10 | 24.99 | 74.96 | 0.05 | | | 600 | 1.22 | 9.76 | 24 |

With regard to respective elements obtained as above, the relationship between the concentration of gas and the resistance value was studied by using the gases obtained by compounding hydrogen, methane or butane with purified air as samples. The results are shown in FIGS. 3 through 22. The relationship between the Figures and respective embodiments is shown in Table 2. In each Figure, the concentration resistance value relationship is represented by line LH for hydrogen, by LM for methane, and by line LB for butane, respectively.

The resistance value was measured by the method described below.

Figure 25:
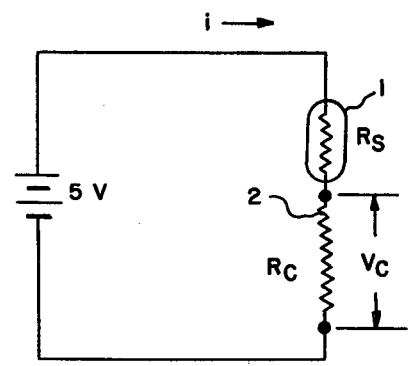
FIG. 25 is a circuit diagram for measuring the resistance value.
Figure 19:
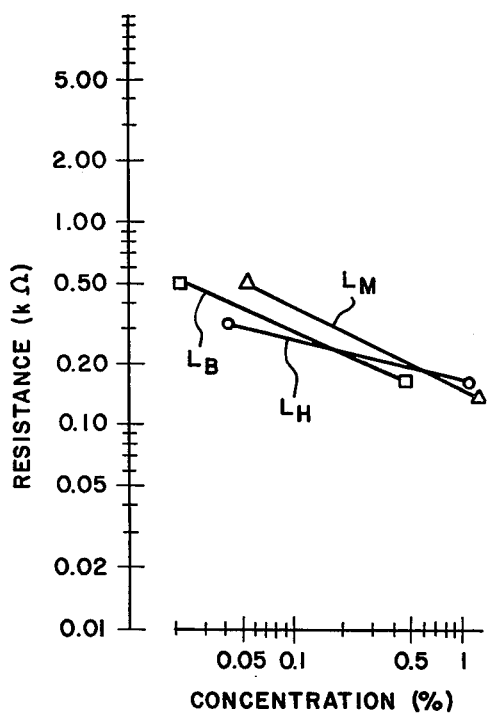
Figure 20:
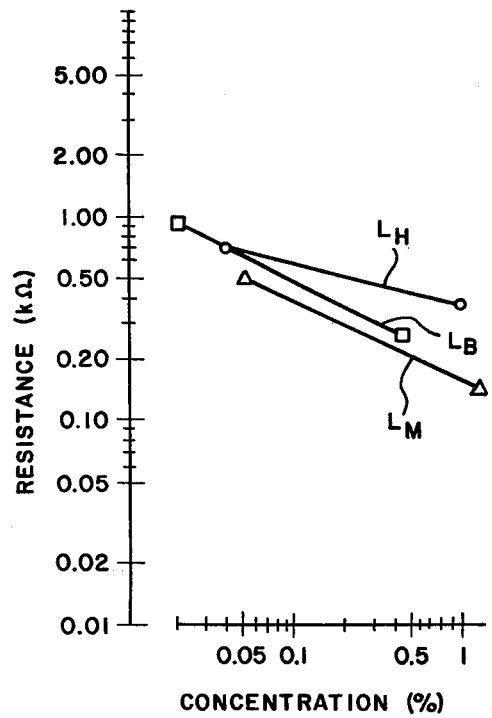
Figure 21:
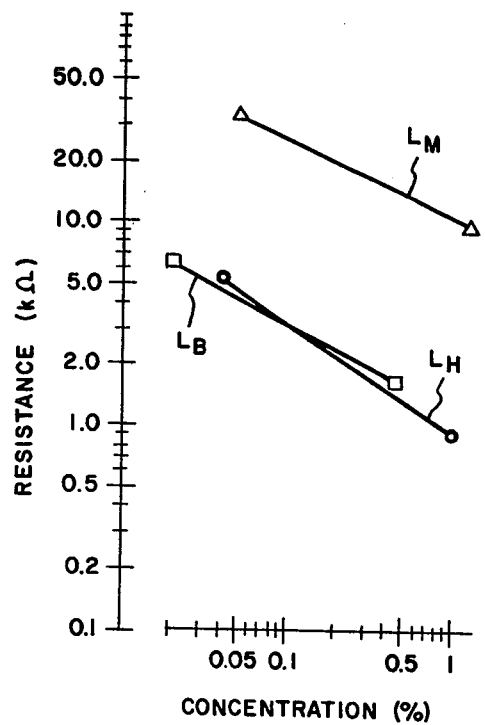
Figure 22:
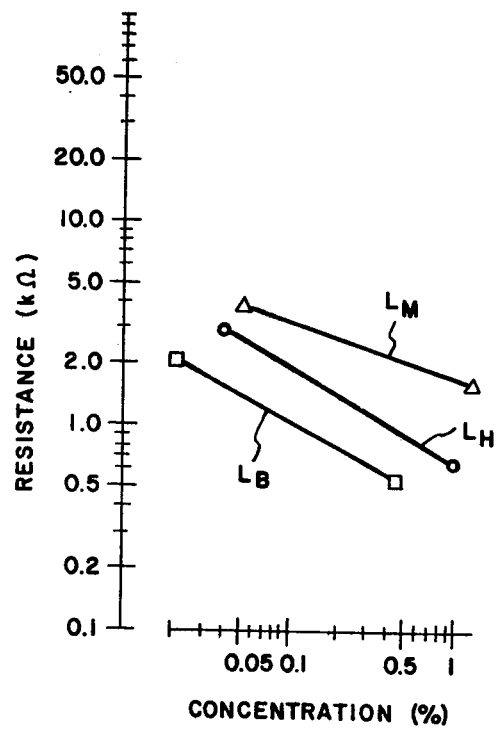
Figure 23:
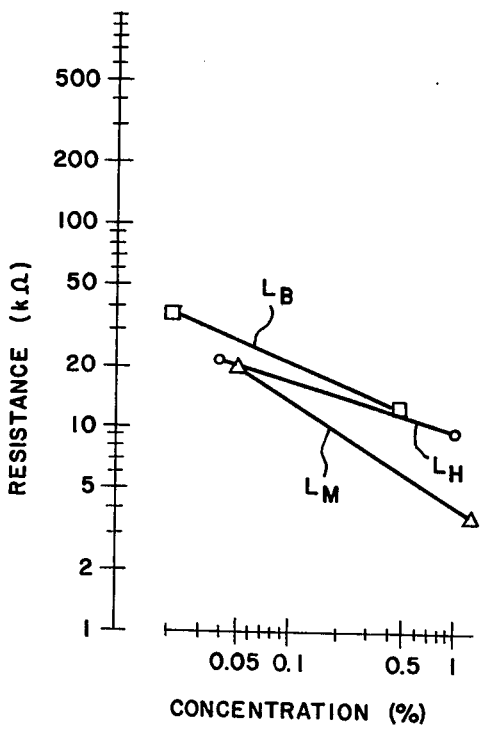
Figure 24:
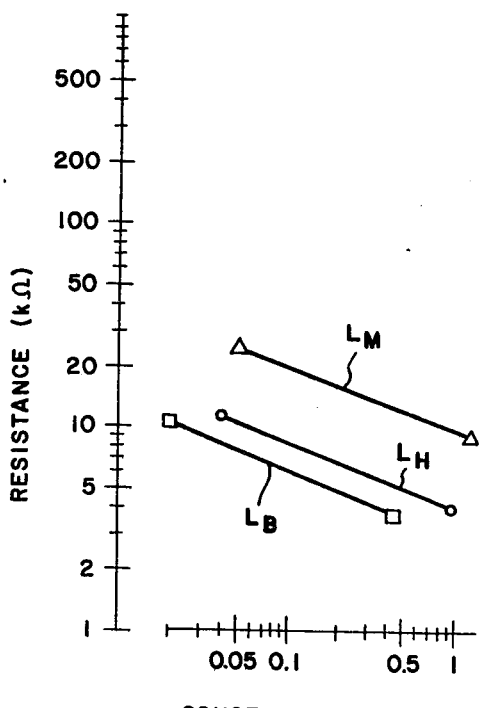
Figure 26:
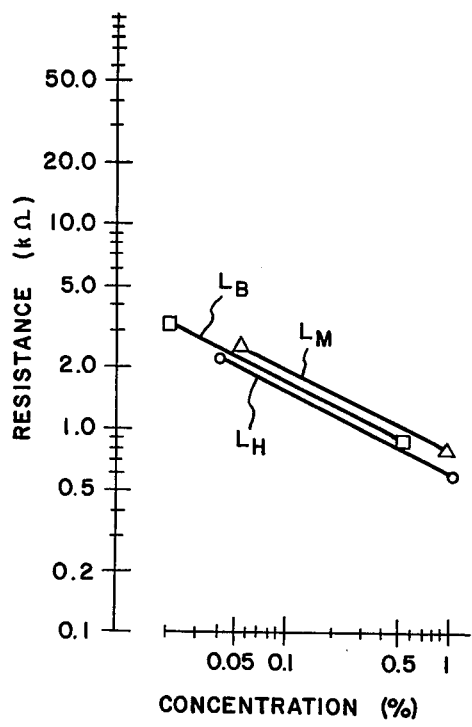
Figure 27:
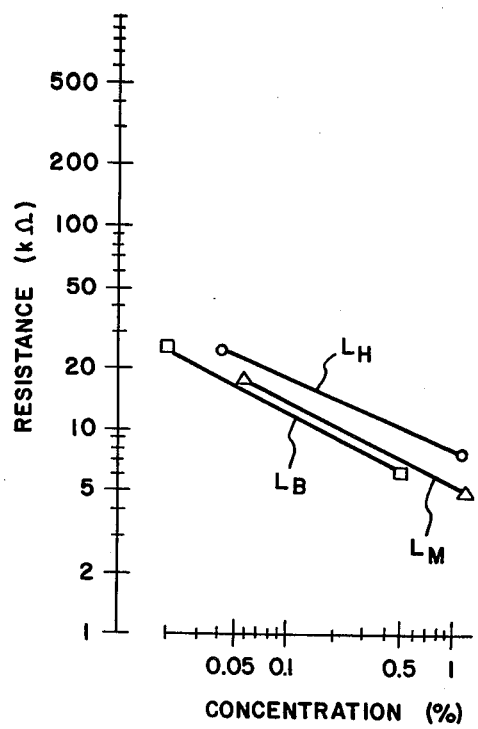
Figure 28:
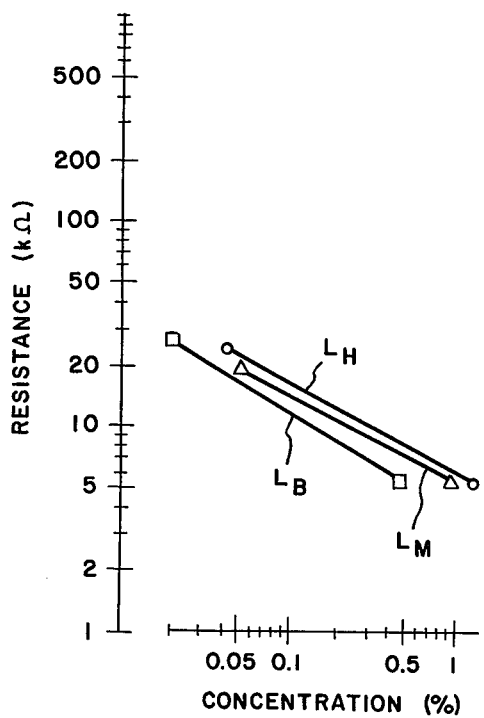
Figure 29:
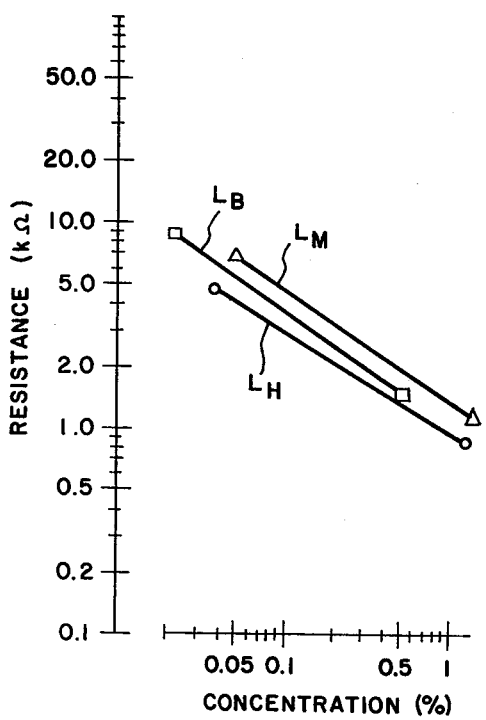
Figure 30:
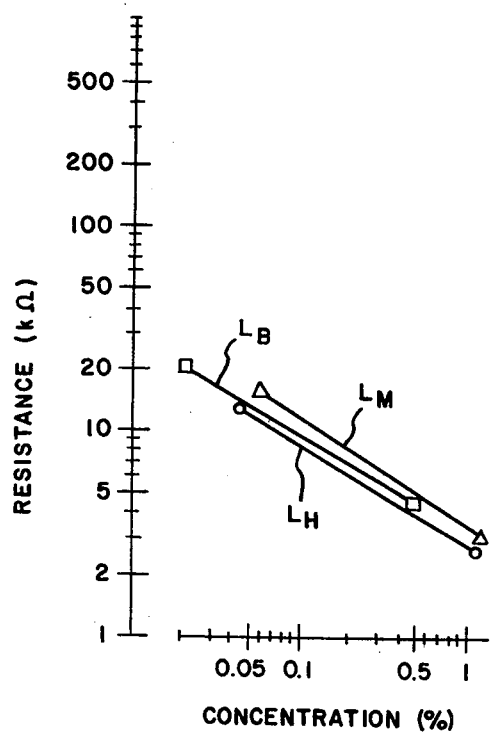
Figure 31:
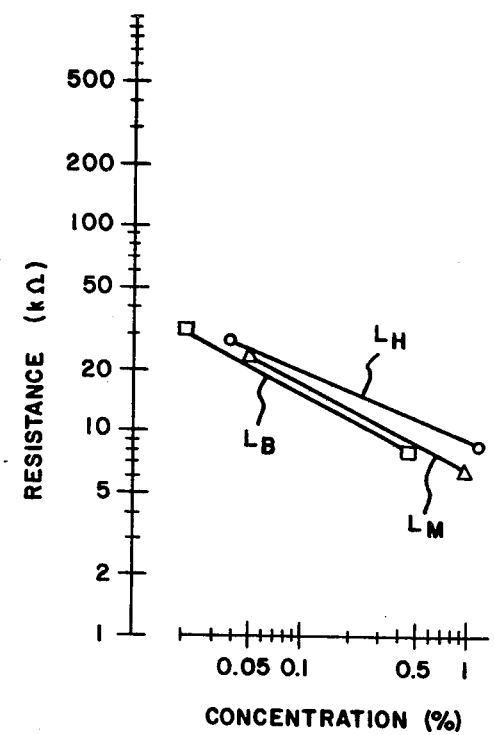
Figure 32:
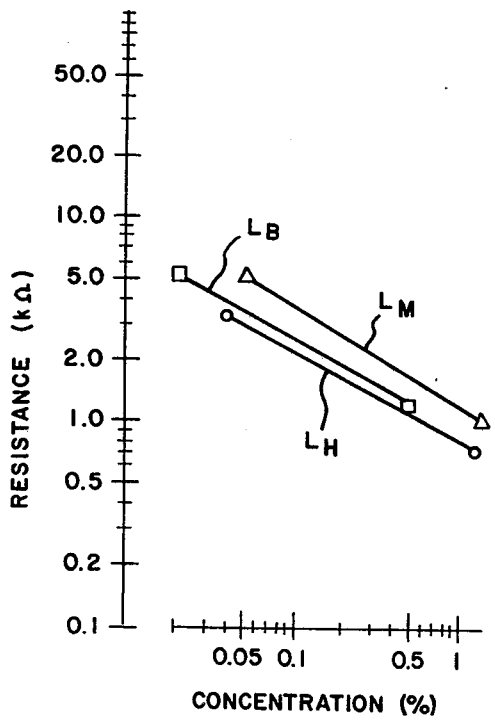
Figure 33:
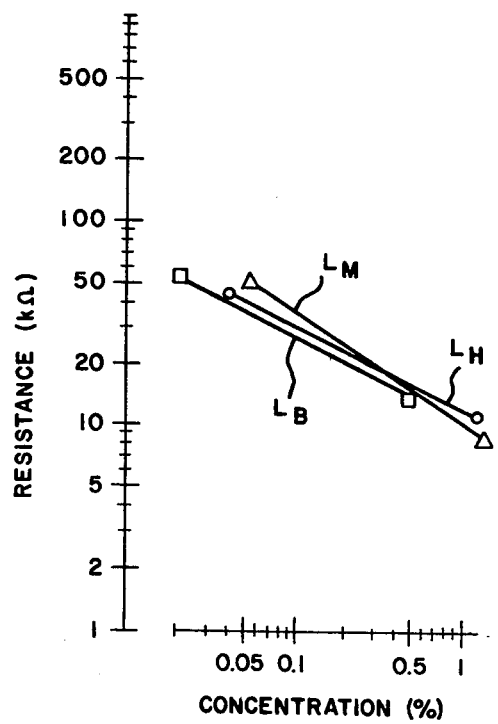
Figure 34:
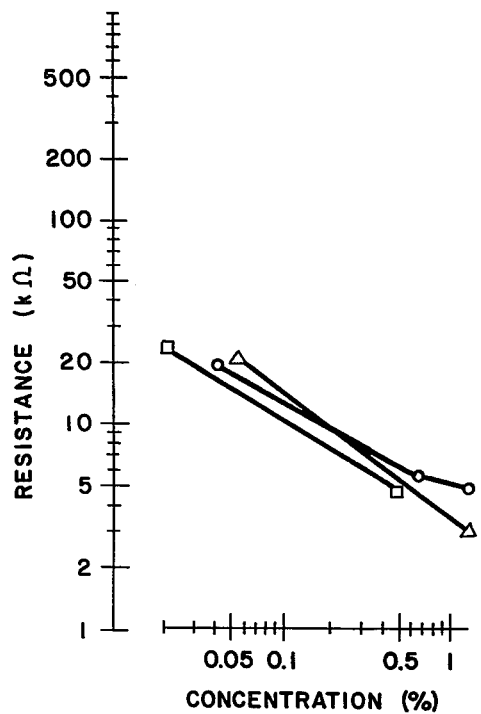
Figure 35:
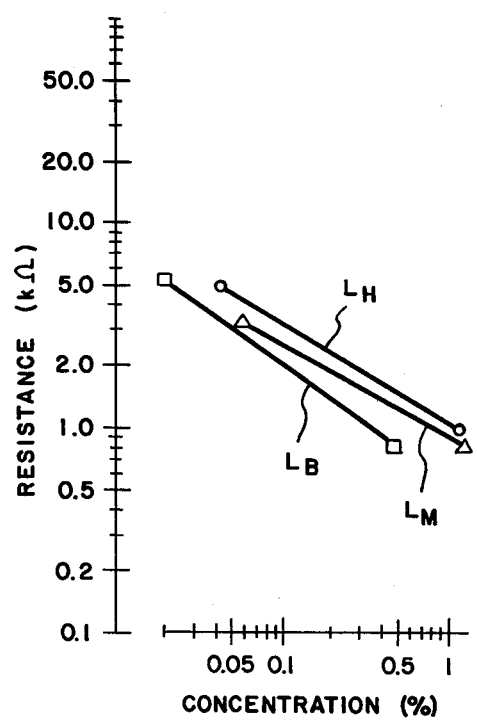
Figure 36:
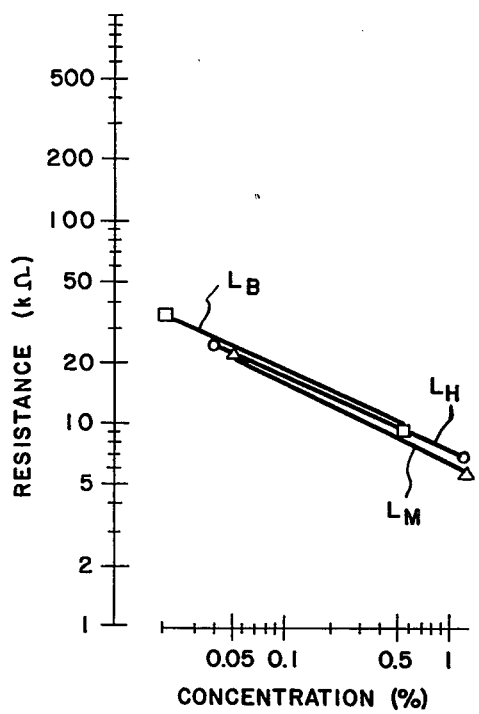
Figure 37:
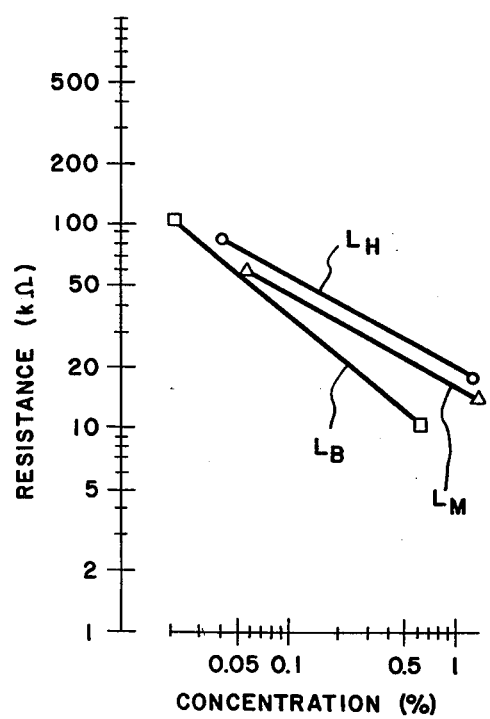
Figure 38:
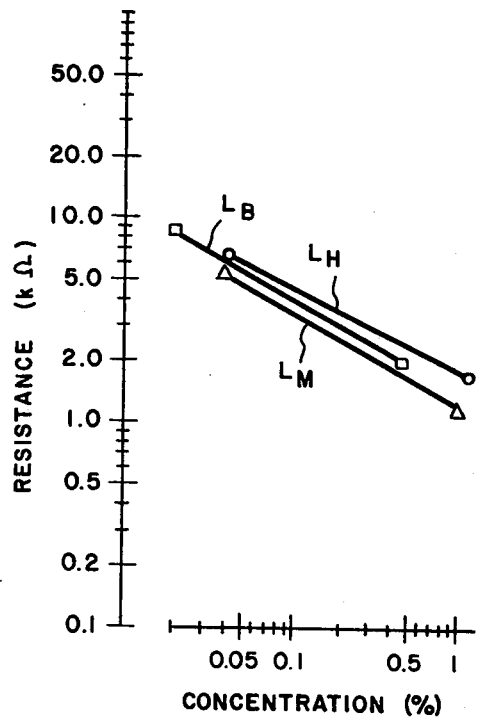
Figure 39:
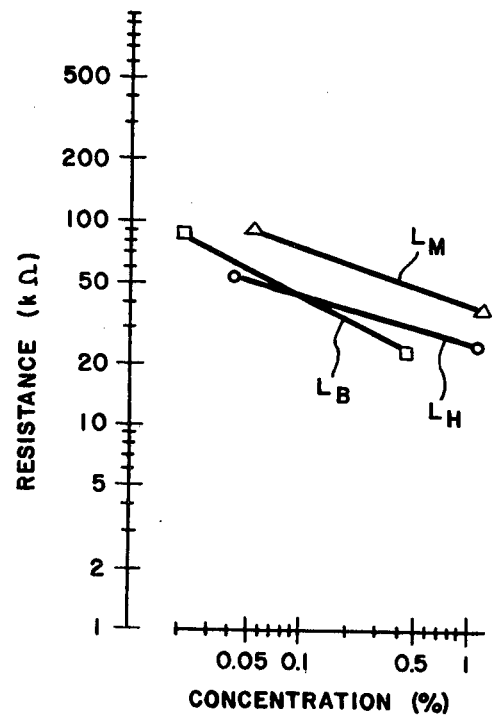
Figure 40:
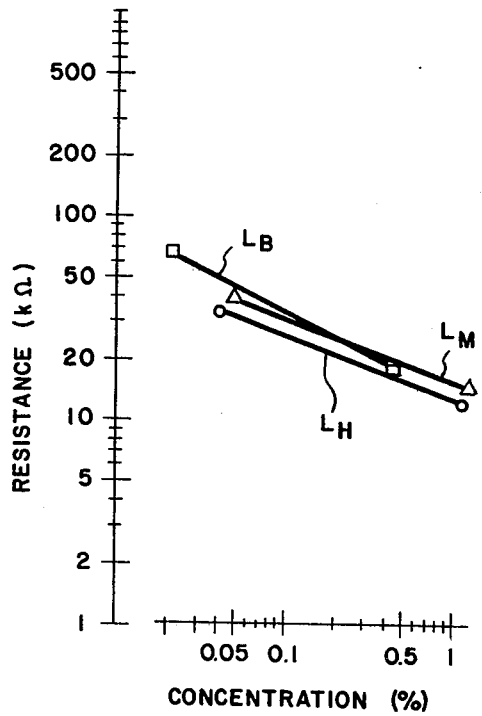

As shown in FIG. 25, a fixed resistor 2 (resistance value of R$_c$Ω) for measuring the resistance was connected in series to the main gas sensing element 1 obtained as above, and to their both ends, 5 V constant voltage was applied. By measuring the electric potential Vc (V) at the both ends of the fixed resistor 2, the resistance value Rs (Ω) of the main gas sensing element 1 can be obtained from the following equation. In this case, i denotes the electric current flowing through the circuit.

$$5 = i(R_s + R_c)$$

$$V_c = i \cdot R_c$$

$$\therefore R_s = R_c \left( \frac{5}{V_c} - 1 \right)$$

First, the purified air with controlled moisture was fed into the measuring tank having the main gas sensing element installed, and the atmosphere was thoroughly stabilized then the resistance value of the element was measured by using the aforesaid method. Next, hydrogen, methane butane were fed into the measuring tank successively, and under a completely stabilized state (about 2 hours later), the resistance values in respective gas atmospheres were measured by the same method. In this case, it is preferable to separate the respective measurements with about one day intervals in order to avoid to leave the trade of each measurement. For the measurement, the temperature of the element was set and maintained at 450° C., through controlling the voltage applied to the heater used for heating the element.

Also, the index E indicating whether the element is working equally to all of hydrogen, methane, and butane, or not, was obtained by using the following equation. The results are shown in Table 2.

$$E = (R_1/R_2)$$

In the equation shown above, $R_1$ denotes the minimum value of resistance values of respective elements with 0.04% in hydrogen, 0.05% in methane, and 0.02% in butane, i.e., 1/100 of the lower explosive limit. $R_2$ represents the maximum value of the resistance values of respective element with 1.0% in hydrogen, 1.25% in methane, and 0.45% in butane, i.e. ¼ of the lower explosive limit.

Moreover, the geometrical mean $\sqrt{R_1 \cdot R_2}$ of the minimum value and the maximum value thus obtained was calculated, and it was shown together in Table 2 as intermediate resistance value.

The overall evaluation of the foregoing results turned out that all of the embodiments were better than the comparison embodiments. That is, the comparison embodiments 1~3 as well as 6~10 are small in E, the comparison embodiments 4 and 5 are too gentle in gradient of the methane concentration-resistance relationship line LM, and the comparison embodiments 5 and 6 are too low in intermediate resistance value.

The another form of the main gas sensing element according to this invention is that, wherein 3 types, i.e., indium oxide, $\alpha$ form ferric oxide (as raw material of $\alpha Fe_2O_3$, $\alpha Fe_2O_3$, $\gamma Fe_2O_3$, $\gamma Fe_2O_3$, $Fe_3O_4$, $\alpha FeOOH$, etc. can be used as far as they give $\alpha Fe_2O_3$ after baking), and pallidium oxide, are used as effective components, and in order to improve the sensitivity as well as balance, said 3 types of components having respective features are mixed for use.

In said $In_2O_3$–$\alpha Fe_2O_3$—PdO system, the intended effects by adding the secondary components are the improvement in resistance value as well as concentration dependence on respective gases, as to $Fe_2O_3$, while said intended effects are the improvement in sensitivity to methane gas, as well as concentration dependence on respective gases, as to PdO.

In the main gas sensing element according to the present invention, the other effects can also be brought about by adding $PtO_2$ or $Rh_2O_3$ as the fourth component. The addition of $PtO_2$ improves the sensitivity to hydrogen gas, and the addition of $Rh_2O_3$ improves the dependence on concentration of respective gases.

The description will be given hereunder on embodiments of said form, as well as on comparison embodiments.

An element, i.e., a gas sensor (sinter) was prepared as follows: as starting powder material, $\alpha Fe_2O_3$ obtained by firing $\alpha FeOOH$ (Toda Kogyo Co., Ltd., Part No. Y-2) at 300° C. for 1 hr. in the air, and $In_2O_3$, PdO, same as those in $In_2O_3$—$SnO_2$—PdO system, were selected; and said materials were compounded in a manner to obtain the element composition ratio same as that in Table 3, shown later; then, after thoroughly mixed (total amount 1 g-30 minutes) in grinder; a specified amount (15 mg) of the mixed powder was weighed out for use; and shaped into cylindrical element with diameter of 2 mm $\phi$, length of 2 mm, and with 2 platinum electrodes (diameter 0.2 mm $\phi$, length 15 mm) embedded in parallel, by comparison forming (pressure 1~2 t/cm$^2$); thereafter, baked at 600° C., 700° C., 750° C., or 800° C., for 1~3 hr, in the air.

The X-ray analysis revealed that respective oxides included in the gas sensor were presented in mixed state. Also, the analysis by using the X-ray microanalyzer showed that respective components were dispersed quite homogeneously. It was confirmed by ESCA (photoelectronic spectroscopic analysis) that there were the cases wherein palladium oxide was partially reduced to metallic palladium. However, in the present invention, said metallic palladium was treated as palladium oxide, and included in palladium oxide for calculating the composition ratio.

A gas sensing unit was prepared by providing a coiled type heater around it, and also covering it with stainless steel wire net cap as a measure for explosion-proof.

For each element thus obtained, the relationship between the gas concentration and the resistance value was studied by using the sample gas prepared by compounding the purified air with hydrogen, methane, or butane. The results are shown in FIGS. 26 through 43. The relationship between said Figures and the embodiment is shown in Table 3. In each Figure, the line LH for hydrogen, the line LM for methane, and the line LB for butane represent the concentration-resistance value relationship of respective components. The resistance value was measured by using the method same as that described previously.

TABLE 3

| | MAIN GAS SENSOR COMPOSITION | | | | | PERFORMANCE | | | |
| --- | --- | --- | --- | --- | --- | --- | --- | --- | --- |
| | | | | FOURTH COMPONENT | | FIRING TEMP. | E | INTERMEDIATE RESISTANCE | FIG. |
| | $In_2O_3$ | $\alpha Fe_2O_3$ | PdO | $PtO_2$ | $Rh_2O_3$ | (°C.) | (—) | VALUE (KΩ) | NUMBER |
| EMBODIMENT 1 | 82.0 | 15 | 3.0 | | | 600 | 2.58 | 1.45 | 26 |
| EMBODIMENT 2 | 79.94 | 20 | 0.06 | | | 600 | 2.01 | 1.16 | 27 |
| EMBODIMENT 3 | 79.0 | 20 | 1.0 | | | 600 | 3.40 | 1.02 | 28 |
| EMBODIMENT 4 | 77.0 | 20 | 3.0 | | | 600 | 3.39 | 2.53 | 29 |
| EMBODIMENT 5 | 74.0 | 20 | 6.0 | | | 600 | 2.93 | 8.03 | 30 |

TABLE 3-continued

| | MAIN GAS SENSOR COMPOSITION | | | | | PERFORMANCE | | | |
|---|---|---|---|---|---|---|---|---|---|
| | | | | FOURTH COMPONENT | | FIRING TEMP. | E | INTERMEDIATE RESISTANCE | FIG. |
| | $In_2O_3$ | $\alpha Fe_2O_3$ | PdO | $PtO_2$ | $Rh_2O_3$ | (°C.) | (—) | VALUE (KΩ) | NUMBER |
| EMBODIMENT 6 | 69.94 | 35 | 0.06 | | | 600 | 2.56 | 1.45 | 31 |
| EMBODIMENT 7 | 64.0 | 35 | 1.0 | | | 600 | 3.09 | 1.92 | 32 |
| EMBODIMENT 8 | 62.0 | 35 | 3.0 | | | 600 | 3.00 | 2.53 | 33 |
| EMBODIMENT 9 | 47.0 | 50 | 3.0 | | | 600 | 3.72 | 9.49 | 34 |
| EMBODIMENT 10 | 44.0 | 50 | 6.0 | | | 600 | 3.56 | 16.38 | 35 |
| EMBODIMENT 11 | 37.0 | 60 | 3.0 | | | 600 | 2.25 | 14.88 | 36 |
| EMBODIMENT 12 | 77 | 20 | 2.0 | 1.0 | | 600 | 3.05 | 3.41 | 37 |
| EMBODIMENT 13 | 62 | 35 | 2.0 | | 1.0 | 600 | 3.02 | 3.28 | 38 |
| COMPARISON EMBODIMENT 1 | 89.94 | 10 | 0.06 | | | 600 | 1.51 | 0.44 | 39 |
| COMPARISON EMBODIMENT 2 | 87.0 | 10 | 3.0 | | | 600 | 1.94 | 0.24 | 40 |
| COMPARISON EMBODIMENT 3 | 80.0 | 20 | 0 | | | 600 | 1.69 | 0.53 | 41 |
| COMPARISON EMBODIMENT 4 | 70.0 | 20 | 10.0 | | | 600 | 1.76 | 4.96 | 42 |
| COMPARISON EMBODIMENT 5 | 27.0 | 70 | 3.0 | | | 600 | 1.88 | 24.25 | 43 |

The main gas sensor according to the present invention is characterized in that, the relative ratio of said 3 types of components is set as follows: 85~40% by weight (hereinafter, abbreviated as %) for indium oxide, 15~60% for iron oxide, 0.06~6% for palladium oxide, and more preferably 80~50% for indium oxide, 20~50% for α form ferric oxide, and 1.0~6.0% for palladium oxide.

Figure 41:
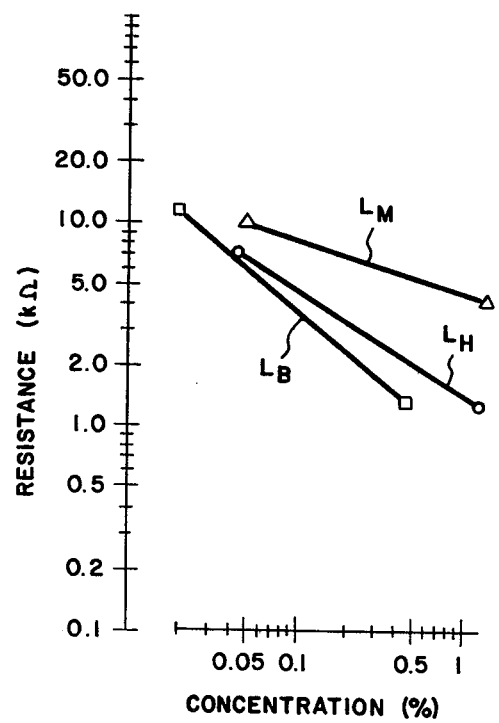
Figure 42:
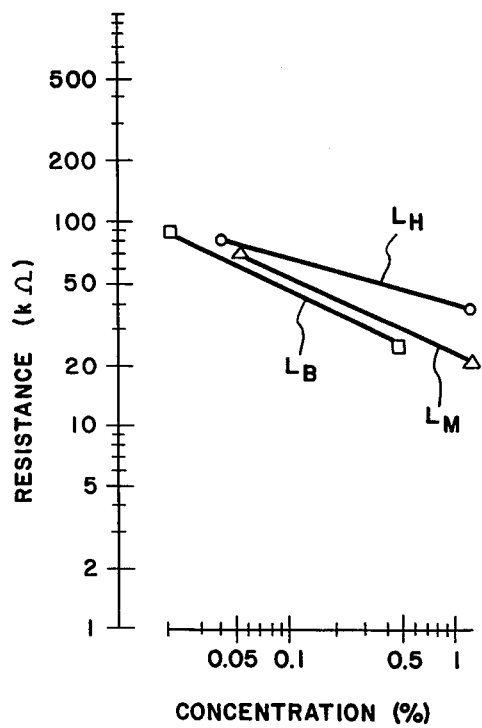
Figure 43:
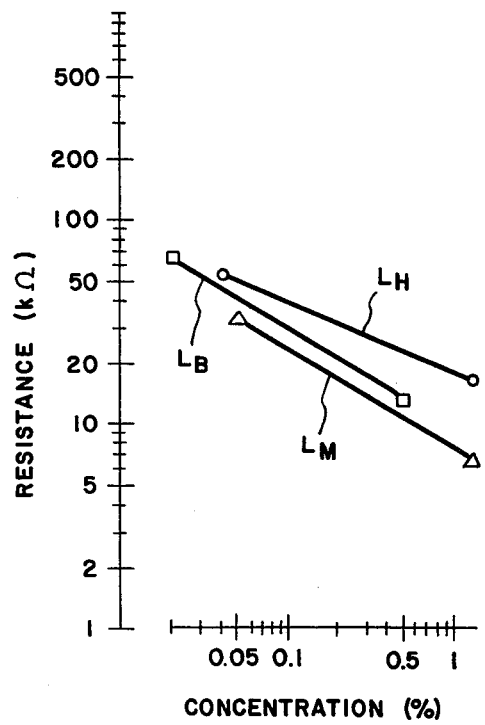

When α form ferric oxide is less than 15%, the element resistance is too small (FIGS. 39 and 40), while when it exceeds 60%, the sensitivity as well as concentration dependence to hydrogen gas decreases, causing the disruption in balance in sensitivity to respective gases, as well as the decrease in E value (FIG. 43). When palladium oxide is less than 0.06%, the sensitivity to methane gas decreases noticeably and the E value also decreases (FIG. 40), while when it exceeds 6.0%, on the contrary, the concentrated dependence on respective gases decreases, ensuring the decrease in E value (FIG. 41).

The present invention provides an alcohol sensor that is effective as auxiliary gas sensor in said gas detection proposed.

The unique features of the alcohol sensor according to the present invention are that its effective components include magnesium oxide, chromium oxide, zirconium oxide, and that the molar ratio of said components is set to have the relationship as shown in an equation below when the molar ratio of each component oxide to the total effective components is represented by Mm for magnesium oxide by Mc for chromium oxide, and by Mz for zirconium oxide.

$$\frac{Mz}{(Mm + Mc) \div 2 + Mz} = 0.01 \sim 0.5$$

Then hereunder, the detailed description will be given on the above.

In the case mentioned above, the effective components mean the components showing the capability to detect the target gas (gas sensing capability).

In the foregoing description, it was stated that said effective components include magnesium oxide, chromium oxide and zirconium oxide, but it is the expression used for the purpose of defining the composition ratio of the element. Consequently, it does not necessarily imply only the gas composed of the mixture of said 3 types of oxides alone. Rather, usually, it may mean that the mixture is obtained as follows: because it is preferable to have magnesium oxide and chromium oxide presenting in state of equi-mol, said oxides become a multiple oxide ($MgCr_2O_4$) in baking stage and zirconium oxide is added in said multiple oxide. Mg and Cr can be partially in the form of compound through reaction as in the foregoing case of $MgCr_2O_4$, or all of them can take the form of mutual reaction product. Furthermore, they can partially be presenting as elements or as compounds other than oxides. On the other hand, their oxides may take various forms of oxide due to the fact that their component elements have the plural types of valencing, and there is no restriction imposed on types of said oxides. Also, in the oxides having the plural types of oxide forms, sometimes one of those forms exists in the element independently as single component type, or sometimes plural types of oxides co-exist in the gas sensing element. The oxide forms referred in this case include those having the non-stoichiometric composition owing to lattice defect, etc.

However, magnesium takes the oxidized form of MgO, while zirconium oxide takes the oxidized form of $ZrO_2$, and chromium oxide usually takes the oxidized form of $Cr_2O_3$. Therefore, in this spcification, in specifying the composition ratio of components forming the effective components, the assumption is set as follows: magnesium oxide takes the oxidized form of MgO; chromium oxide is presently in a form of $Cr_2O_3$; and zirconium oxide takes the form of $ZrO_2$ as oxide. Then, under said assumption, it is necessary that the composition ratio of the foregoing 3 types of oxides be set as that represented by the equation shown above. The description with reference to the embodiments will be as follows. In said equation, the maximum value (0.5) in the range (0.01~0.5) possible for the equation value to take is obtained when, for example, the molar ratio of each of said 3 types of oxides is ⅓. On the contrary, the minimum value (0.01) is nearly reached when, for example, the molar ratio of both magnesium oxide and chromium oxide is 0.4975, and that of zirconium oxide is 0.005.

When zirconium oxide is absent, the sensitivity to alcohol lowers, and also in relative sensitivity compared with that to butane gas, the sensitivity to alcohol gets inferior. Also, the mechanical strength of the element decreases. On the other hand, when magnesium oxide exceeds chromium oxide in quantity, in addition to decrease in resistance value of the element, the alcohol sensitivity tends to be lowered. As mentioned above, the components contained in effective components take the form of mutual reaction products, such as multiple oxide, or element, or compound other than oxide. However, even in such case, for calculation of composition ratio, they are assumed to have the aforesaid oxidized forms, such as that 1 mole of $MgCr_2O_4$ is a combination of 1 mole of $MgO$ with 1 mole of $Cr_2O_3$.

In preparation of gas sensing element, sometimes, the component acting as binder, that serving as extender, etc. are added to the components showing the capability of sensing gases. However, such cases also are included in the scope of this invention as far as their gas sensing components meet the specification defined as above. The reason for that, in this specification, only the effective components are selected for definition as mentioned above is nothing but the result of the consideration on the frequent practice of adding the components other than the gas sensing components other than the gas sensing components during actual preparation of the gas sensor element. Such statement however, does not imply the exclusion of the cases wherein the gas sensing element is composed solely of the effective components as mentioned above, and said cases are needless to say, included in the scope of this invention.

The alcohol sensing element as auxiliary gas sensing element according to this invention has the property to show the increase in resistance with increase in gas concentration, and accordingly, when it is installed in detection circuit in FIG. 1 as auxiliary gas sensing element, the inverter I is unnecessary.

Figure 44:
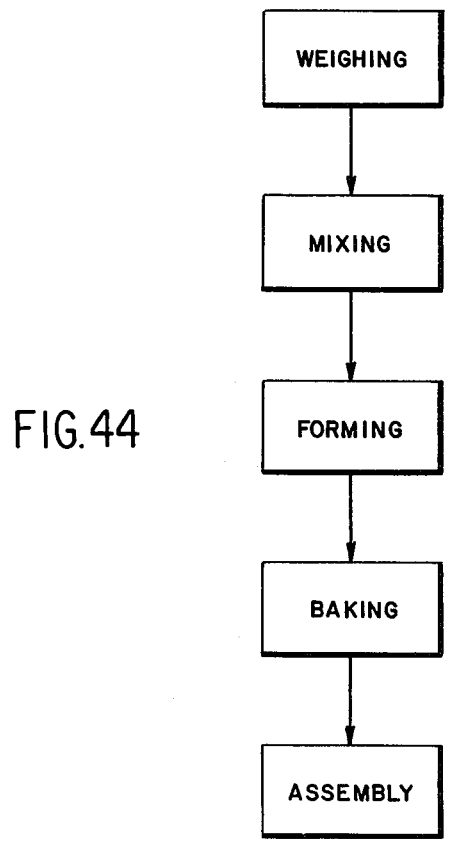
FIG. 44 shows a process diagram for preparing an alcohol sensing element according to this invention.
Figure 45:
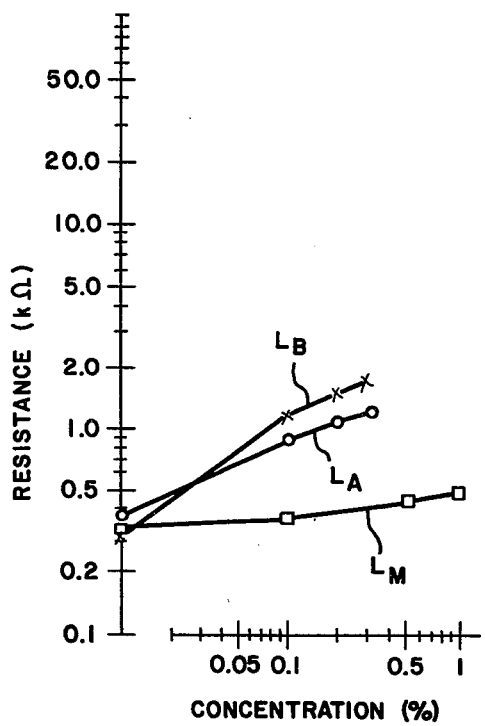
Figure 46:
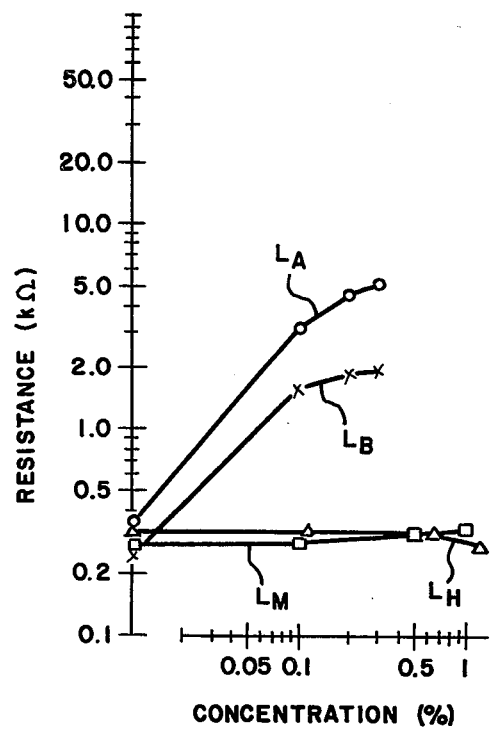
Figure 47:
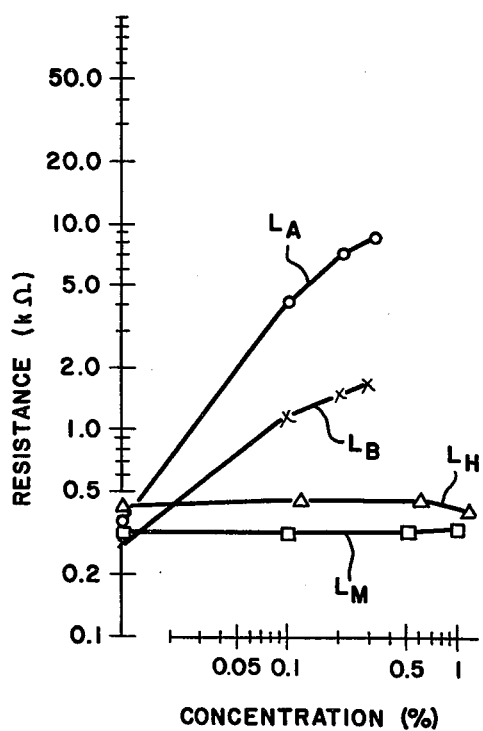
Figure 48:
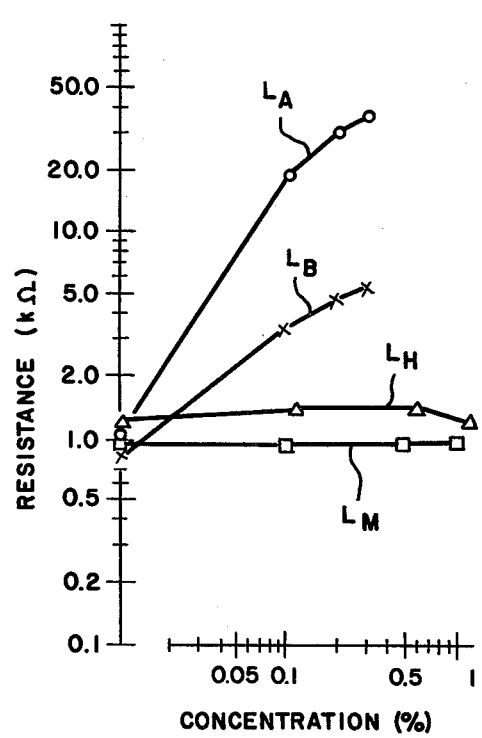

The alcohol sensing element according to this invention is prepared, for example, by the following processes. FIG. 44 shows the process diagram for it. As shown in said diagram, first, the starting materials are weighed out for compounding. Material for MgO and material for $Cr_2O_3$ are weighed out so that MgO and $Cr_2O_3$ become equi-mole, and the material for $ZrO_2$ is weighed out so that a specified amount is compounded. In this case, it is preferable to select the raw materials taking the form of the desired oxides, i.e. MgO, $Cr_2O_3$, and $ZrO_2$, but it is not always necessary to do so. In short, as far as they finally give the alcohol sensing element with foregoing composition, any raw material can be used.

Then, the raw materials for compounding are mixed by using the grinder. Preferred time for mixing is more than 30 minutes.

After mixing, the raw material mixture is formed into a specified shape. The forming is carried out, for example, by press forming into cylindrical shape (diameter $\phi$ 2 mm, height 2 mm) with 2 platinum wires ($\phi$ 0.2 mm, length 15 mm) embedded in parallel, by using a small size press.

The formed body thus obtained is then, for example, placed in heat-resisting porcelain container, and baked at the temperature about 1000° C. in the air, by using an electric oven. Sometimes, prior to forming, the preliminary baking is performed to change magnesium oxide and chromium oxide into the form of $MgCr_2O_4$, but usually, said pre-baking is omitted, and only the glost firing is used.

The element usually made to take the form of sinter for purposes to readily obtain the high gas sensitivity as well as high stability agains time lapse, etc., but the form is not limited to the above, and it can be a thick film, thin film, or any other forms.

The element thus obtained is assembled into a specified alcohol sensing element through spot-welding the platinum electrodes to terminal board equipped with heater, and covering it with stainless steel explosion-proof net.

According to the analysis of gas sensor by X-ray diffraction, most of magnesium oxides and chromium oxides had reacted into $MgCr_2O_4$. However, chromium oxide as reaction residue was also detected.

Next, the description will be given on the embodiments as well as on comparison embodiments.

The alcohol sensing element was made by using the method described above, after compounding the raw materials with arrangement to obtain the composition of the element as shown in Table 4. The baking conditions were as follows: 1300° C. in baking temperature; 5 hrs. for about 1100° C. in baking time; the air for baking atmosphere; and gradual heating-gradual cooling for baking state.

TABLE 4

| | ELEMENT COMPOSITION (MOLAR RATIO) | | | FIG. NUMBER |
|---|---|---|---|---|
| | $ZrO_2$ | MgO | $Cr_2O_3$ | |
| COMPARISON EMBODIMENT | 0 | 100/200 | 100/200 | 45 |
| EMBODIMENT 1 | 5/195 | 95/195 | 95/195 | 46 |
| EMBODIMENT 2 | 10/190 | 90/190 | 90/190 | 47 |
| EMBODIMENT 3 | 20/180 | 80/180 | 80/180 | 48 |

As to respective elements obtained as above, the relationship between gas concentrated and resistance value was checked by using the sample gas prepared by compounding alcohol vapor, hydrogen, methane, or butane, with purified air. The results are shown in FIGS. 45-48. The relationship between said Figures and respective embodiments is shown in Table 4. In each Figure, lines LA, LH, LM, represent the concentration-resistance value relationship for hydrogen, methane, and butane, respectively, in said order.

The resistance value was measured by the method same as that for target gas sensing element (FIG. 25).

It should be apparent from the foregoing experimental results that the alcohol sensing element according to this invention is high in gas detecting sensitivity to alcohol vapor, while, in comparison with it, the detecting sensitivity to the other gases is strikingly low.

We claim:

1. A gas detector comprising:
   a main signal processing unit, including: a main gas sensing element for sensing a change in electric resistance to both a detection target and non-target gases and outputing a first alarm driving signal by detecting a target or nontarget gas exceeding a first specified level;
   a sub-signal-processing unit including: a circuit unit coupled to said main gas sensing element for outputing a second alarm driving signal by detecting gas exceeding a second level of concentration set at lower than the first specified level, an auxiliary gas sensing element showing a change in electrical resistance particularly in response to a non-target gas a gate signal trigger unit coupled to said auxiliary gas sensing element for blocking the second alarm driving signal, by detecting non-target gas with a concentration exceeding a third specified level;

an alarm triggering means that is actuated in response to the first or second driving alarm signal; and said auxiliary gas sensing element being made from magnesium oxide, chromium oxide, zirconium oxide wherein the molar ratios of magnesium oxide Mm, chromium Mc, zirconium oxide Mz are:

$$\frac{Mz}{\frac{Mm + Mc}{2} + Mz} = 0.01 \simeq 0.5.$$

2. A gas detector as set forth in claim 1, wherein said main gas sensing element is the metallic oxide sinter containing indium oxide, one type selected from a group composed of tin oxides and α form ferric oxides, and palladium oxide.

3. A gas detector as set forth in claim 1, wherein said main gas sensing element is the metallic oxide sinter containing indium oxide, tin oxide and palladium oxide with ratio's of 25~50%, 75~50%, 0.06~5.0% by weight, respectively.

4. A gas detector as set forth in claim 1, wherein said main gas sensing element contains indium oxide, tin oxide, and palladium oxide, with ratio's of 35~45%, 65~55%, 0.06~5%, respectively.

5. A gas detector as set forth in claim 1, wherein said main gas sensing element is the metallic sinter, containing indium oxide, α form ferric oxide and palladium oxide, with ratio's of 85~40%, 15~60%, 0.06~6%, respectively.

6. A gas detector as set forth in claim 1, wherein said main gas sensing element is the metallic oxide sinter, containing indium oxide, α form ferric oxide, and palladium oxide, with ratio's of 85~50%, 20~50%, 1.0~6.0%, respectively.

7. A gas detector as set forth in claim 1, wherein the main gas sensing element further contains platinum oxide.

8. A gas detector as set forth in claim 1, wherein the main gas sensing element further contains rhodium oxide.

* * * * *